United States Patent [19]

Gaasterland et al.

[11] Patent Number: 5,372,595
[45] Date of Patent: Dec. 13, 1994

[54] CONTACT PROBE FOR LASER CYCLOPHOTOCOAGULATION

[75] Inventors: Douglas E. Gaasterland, Potomac, Md.; David M. Buzawa, San Jose, Calif.

[73] Assignees: Georgetown University, Washington, D.C.; Iris Medical Instruments, Inc., Mountain View, Calif.

[21] Appl. No.: 133,953

[22] Filed: Oct. 7, 1993

Related U.S. Application Data

[63] Continuation of Ser. No. 668,644, Mar. 13, 1991, abandoned.

[51] Int. Cl.⁵ ............................................. A61M 5/06
[52] U.S. Cl. ......................................... 606/4; 606/13; 606/16
[58] Field of Search ........................... 606/2–6, 606/10–19; 128/897

[56] References Cited

U.S. PATENT DOCUMENTS 2,033,397 3/1936 Richman .............................. 606/50

FOREIGN PATENT DOCUMENTS 508984 12/1972 U.S.S.R. .

OTHER PUBLICATIONS

"Transcleral Ruby Laser Irradiation of the Cilliary Body in the Treatment of Intractable Glaucoma" by Beckman et al.; Tr. Am. Acad. Ophth. & Otol.; vol. 76, Mar.–Apr. 1972 pp. 423–436.

"Laser Cyclophotocoagulation" by Schuman et al. International Ophthamol Clinics: vol. 30, No. 2 1990.

"Rule Placement & Power Levels in Contact Transscleral Nerodymonium YAG Cyclocoagulation"; Arch Ophthamol vol. 108 May 1990.

*Primary Examiner*—David M. Shay
*Attorney, Agent, or Firm*—Townsend and Townsend Khourie and Crew

[57] ABSTRACT

A fiber optic handpiece has portions formed with special contours that facilitate consistent placement of the probe in an axial rather than radial orientation, thus decreasing the likelihood of incidental laser exposure to unintended structures while maintaining the intrinsically higher laser-tissue coupling efficiency of a contact technique. One particular embodiment incorporates features that permit rapid and consistent positioning relative to visible landmark structures such as the limbus, thereby reducing treatment variability.

6 Claims, 2 Drawing Sheets

CONTACT PROBE FOR LASER CYCLOPHOTOCOAGULATION

This is a continuation of application Ser. No. 07/668,644 filed Mar. 13, 1991, now abandoned.

BACKGROUND OF THE INVENTION

This invention relates generally to eye surgery and more particularly to fiber optic handpieces used for laser eye surgery.

The treatment of glaucoma and its symptoms has resulted in a wide variety of approaches. Surgical treatment methods include the use of cryotherapy, ultrasound, microwave heating, microsurgery and a number of laser wavelengths and target structures. Much recent laser glaucoma treatment has concentrated on techniques to reduce aqueous production and intraocular pressure by selective destruction of the ciliary body and related processes. The ciliary processes include the ciliary muscle and the blood vessels within the ciliary body. The term ciliary body is hereinafter to be understood to refer to the ciliary body as a whole and its related processes. Infrared lasers, predominantly Nd:YAG lasers operating at 1.06 μm, have been used to deliver laser energy of a few joules per treatment site. Laser delivery for such cyclophotocoagulation has been accomplished both by free beams directed through air to a patient seated at a special slit lamp and by fiber optic handpieces placed in contact with the patient's eyeball. Handpieces have been used both with and without beamshaping contact tips.

These techniques have advantages as well as drawbacks to their widespread clinical use. Delivery of a freely propagating laser beam to a patient seated at a slit lamp has higher clinical safety margins than with other techniques. This is notable, since thermal damage to the lens has been commonly encountered by researchers applying laser energy in the region of the ciliary body. Drawbacks to the slit lamp technique are several. Since the ciliary body targets are not visible to the doctor during the procedure, aiming of the laser is by visual estimation, which contributes to variation in result from patient to patient and from doctor to doctor. Also, clinical efficiency of free beam delivery through air is less than that of contact methods, as tissue coupling efficiency is reduced by 10–50%.

Current contact handpieces deliver laser energy via a fiber optic, usually held by the surgeon normal to the surface of the eyeball at a point immediately above the ciliary body. Laser access to the ciliary body is good, but inadvertent thermal damage to the crystalline lens is an undesirable side effect typical to this method. The laser contact method is more efficient than the noncontact method, however, accomplishing similar results with less laser energy, thus affording the possibility of using more compact laser sources. Additionally, direct placement of the laser handpiece against the eyeball makes positioning easier and more consistent than with a slit lamp.

SUMMARY OF THE INVENTION

The present invention provides a fiber optic handpiece and method of use for contact cyclophotocoagulation. The present invention provides substantially all the advantages and none of the disadvantages of prior art techniques.

Briefly, the main advantage of the present invention results from the recognition that the higher clinical safety margins of the slit lamp treatment method are a consequence of the direction of the laser beam being coaxial with the eye's optic axis; contact cyclophotocoagulation in accordance with the present invention is performed with the laser beam directed parallel to the eye's optic axis.

A handpiece according to the present invention has portions formed with special contours that facilitate consistent placement of the probe in an axial rather than radial orientation, thus decreasing the likelihood of incidental laser exposure to unintended structures while maintaining the intrinsically higher laser-tissue coupling efficiency of a contact technique. One particular embodiment incorporates features that permit rapid and consistent positioning relative to visible landmark structures such as the limbus, thereby reducing treatment variability.

A further understanding of the nature and advantages of the invention may be realized by reference to the remaining portions of the specification and the drawings.

DETAILED DESCRIPTION OF THE INVENTION

As mentioned, current contact handpieces deliver laser energy through a fiber optic usually held by a surgeon normal to the surface of the eyeball at a point immediately above, or proximal, the ciliary body. Laser beam direction in this modality is therefore, nearly radial. Laser access to the ciliary body is good, but the radial propagation direction jeopardizes structures adjacent to and near the ciliary body targets. Inadvertent thermal damage to the crystalline lens is an undesirable side effect with this method, as mentioned earlier. Delivery of a freely propagating laser beam to a patient seated at a slit lamp forces the surgeon to apply laser energy in a direction essentially coaxial with, but offset from, the optic axis of the eyeball. This aiming condition, a fortuitous result of a clinical device designed for one procedure being adapted for an entirely new application, allows laser access to the ciliary body while keeping other important structures, e.g. the crystalline lens, out of the direct beam path, increasing clinical safety margins.

Figure 1:
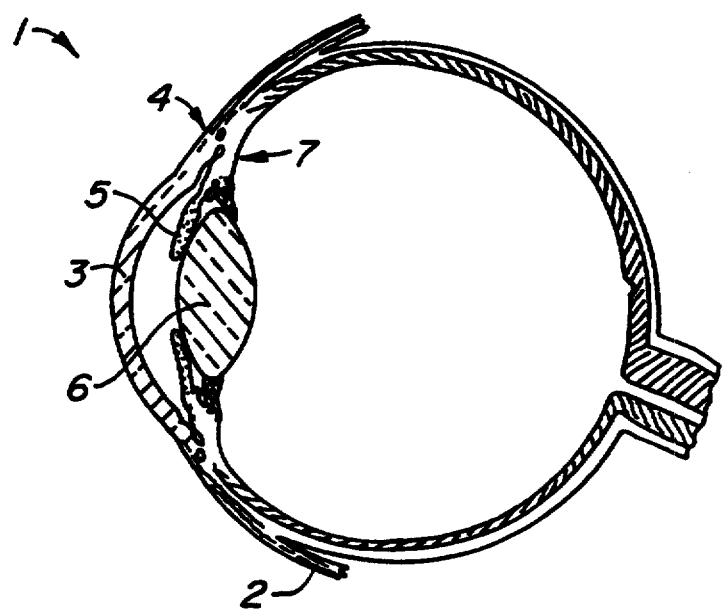
FIG. 1 is a cross-sectional side view of a human eyeball.

FIG. 1 shows an adult human eye, 1, with relevant parts labeled. The sclera, 2, is a tough sheath around the eye which meets the cornea, 3, at a circular junction called the limbus, 4. Behind the cornea lie the iris, 5, the lens, 6, and the ciliary body and related processes, 7. Over the cornea and part of the sclera lies the conjunctiva, 8.

Figure 2:
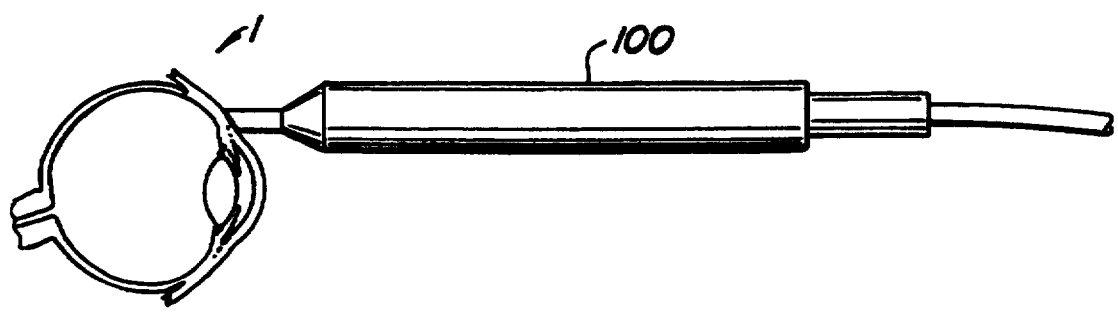
FIG. 2 is a side view of a fiber optic handpiece in accordance with a particular embodiment of the present invention, shown positioned against an eye.

A fiber optic handpiece 100 in accordance with the present invention is shown in FIG. 2 positioned against an eye 1. The output tip of the handpiece has a contact surface contoured to register against the eye at the limbus, with the handpiece aligned so as to direct laser energy parallel to the eye's optic axis.

Figure 3A:
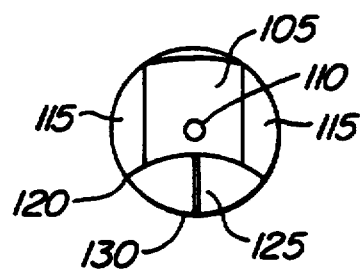
FIGS. 3A, 3B and 3C are a front, side and top views, respectively, of a particular embodiment of the present fiber optic handpiece invention.
Figure 3B:
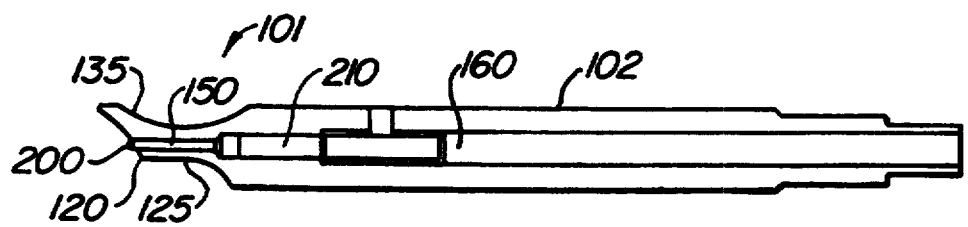
Figure 3C:
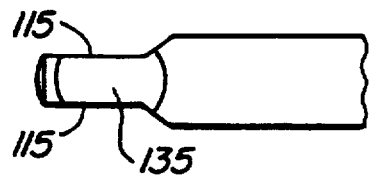

FIGS. 3A, 3B and 3C are front, side and top views, respectively, of a particular embodiment of the present invention as directed to a fiber optic handpiece. Mention will be made to the top, bottom, and sides of the device, which gets rotated about during use. Such references shall refer to its typical position when properly registered at 12:00 on a patient's eye. In FIG. 3A, all of the visible surfaces are part of the output tip. A contact surface, or end surface, 105 contains an opening 110 for the fiber optic and is contoured to conform to the shape of the eye at the limbus when the axis of the handpiece is parallel to the optic axis of the eye. This can be very closely approximated as a concave spherical section of radius 12.5 mm to 12.7 mm, the spherical center being located about 6.7 mm to 6.9 mm below the opening for the fiber optic. With the contact surface so shaped, correct alignment of the handpiece, as in FIG. 2, is made easier.

The width of contact surface 105 is determined by side reliefs 115. In one particular embodiment, in which the fiber opening is equidistant from either side of the contact surface, this half width is chosen to be roughly equal to the desired treatment site spacing. After a first site is treated, each successive site can be selected by aligning a side edge of the probe contact surface with the lesion created at the previous site. In its simplest form, one lateral edge may be a treatment spacing edge; used in the above described manner the distance between treatment sites would be equal to the distance between the treatment spacing edge and the fiber optic. The side relief must extend back from the treatment spacing edge so that it is visible during use.

Along the bottom of the contact surface is a lower surface having a placement edge 120 with a placement contour 125 extending away from the placement edge to the body of the handpiece. This placement edge is shaped to conform to the limbus, circularly concave with a radius of about 5.5-6.0 mm and about 1.2 mm from opening 110 at its closest approach; it can thus be used to facilitate optimal alignment of the probe's fiber optic with the eye's ciliary body. An alignment groove 130 is cut into placement contour 125 and indicates the lateral position of opening 110.

In FIG. 3B output tip 101 and handpiece body 102 are indicated generally. An eyelid lifting contour 135 is shown as a circular concavity in an upper surface, with a radius about 25 mm and a center of curvature located about 31 mm above the axis of the handpiece. The eyelid lifter may be any generally concave or scoop shaped relief of roughly the same size. Placement contour 125 is shown to extend away from placement edge 120, and an unsleeved fiber optic 200 is shown within a narrow bore 150 extending slightly out from the contact surface. The output tip of fiber optic 200 is normally polished flat. When the contact surface is registered against the eye, the protruding fiber optic indents the surface of the eye at that point, squeezing out extracellular water and improving the transmission efficiency of the laser beam. This protrusion may be anywhere from about 0.5 mm to about 1.0 mm, and in the particular embodiment shown is 0.75 mm. Also shown is a sheathed fiber optic portion 210 within a wide bore 160. Side reliefs 115 are shown in more detail, along with eyelid lifter 135, in FIG. 3C.

Figure 4:
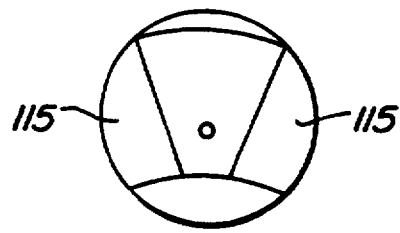
FIG. 4 is a front view of another particular embodiment of the present fiber optic handpiece invention.

It is to be understood that the above description is intended to be illustrative and not restrictive. Many embodiments will be apparent to those of skill in the art upon reviewing the above description. For instance, instead of being parallel as in FIG. 3A, the lateral edges of the contact surface may be as shown in FIG. 4. In FIG. 4 the lateral edges are aligned as ray segments from the optic axis of the eye. They may still be used as treatment spacing edges, and they also aid in the visual alignment of the handpiece around the eye. Additionally, the fiber optic could be equipped with a beamshaping surface, contour, device or crystal tip, and such might also extend past the contact surface instead of the fiber optic itself. The scope of the invention should, therefore, be determined with reference to the appended claims, along with the full scope of equivalents to which such claims are entitled.

What is claimed is:

1. A contact fiber optic handpiece characterized by an axis and adapted to receive a fiber optic for laser surgery on a patient's eye, said eye having a shaped sclera, a limbus, and a optic axis, said contact fiber optic handpiece comprising portions defining a contact surface conforming to the shape of the sclera at the limbus when the axis of the handpiece forms a predetermined angle relative to the optic axis of the eye, wherein the contact surface conform to the shape of the sclera at the limbus when the axis of the handpiece is parallel to the optic axis of the eye.

2. A contact fiber optic handpiece adapted to receive a fiber optic for laser surgery on an eye and having an input end, an output end, a top, a bottom, and sides, said fiber optic having an optic axis, said eye having a shaped sclera, limbus, and an optic axis, said contact fiber optic handpiece comprising:
   a) a body for holding the fiber optic; and
   b) a contoured end portion comprising an end surface having an opening for the fiber optic, said end surface conforming to the shape of the sclera at the limbus when the optic axis of the fiber optic is parallel to the optic axis of the eye.

3. A contact fiber optic handpiece as in claim 2 wherein said contoured end portion further comprises a lower surface sharing a placement edge with the end surface, said placement edge conforming to the shape of the limbus and having a closest approach of about 1.2 mm to the fiber optic opening said lower surface extending from the placement edge so that the placement edge is visible during use.

4. A contact fiber optic handpiece as in claim 3 wherein the contoured end portion is further characterized by
   i) an upper surface having an eyelid lifting portion,
   ii) a lateral treatment spacing edge distanced from the fiber optic opening by about a desired separation of treatment sites, and
   iii) means for aiding the alignment of an axis of the handpiece body with the optic axis of the eye.

5. A contact fiber optic handpiece adapted to receive a fiber optic for laser surgery on an eye and having an input end, an output end, a top, a bottom, and sides, said fiber optic having a beam output tip, said eye having a shaped sclera, a limbus, and an optic axis, said contact fiber optic handpiece comprising:
   a) a generally cylindrical body having a bore with a large diameter portion for holding a sleeved portion of the fiber optic and a small diameter portion at the output end for holding an unsleeved end portion of the fiber optic;

b) portions defining, a contact surface at the output end, wherein
   i) the beam output tip of the fiber optic protrudes about 0.75 mm beyond the contact surface, and
   ii) the contact surface is spherically concave with a radius of curvature about 12.5 mm with a center of curvature located about 6.9 mm below an axis of the output end of the fiber optic;
c) portions defining a placement contour at the bottom of the output end, circularly concave at least at a placement edge shared with the contact surface, with a radius of curvature of about 5.7 mm and a center of curvature located about 6.9 mm below the axis of the output end of the fiber optic, the placement contour extending from the placement edge a sufficient distance for visibility during use;
d) portions defining an eyelid lifting contour on the top of the output end, comprising a cylindrically concave relief with a radius of curvature of about 12 mm with a cylindrical axis extending from side to side about 14 mm above the axis of the fiber optic and about 15 mm toward the input end from a center of curvature of the contact surface; and
e) two side reliefs, one on each side of the output end, extending from the contact surface a sufficient distance for visibility during use, inset into the output end a distance such that the contact surface has a width through the fiber opening substantially equal to twice a desired separation between treatment cites.

6. A contact fiber optic handpiece as in claim 5, wherein the side reliefs have substantially planar portions extending from edges shared with the contact surface, with planes of said substantially planar portions intersecting at a line which passes through the center of curvature of the contact surface and is parallel to the optic axis of the eye.

* * * * *